United States Patent [19]

Hoeksema

[11] Patent Number: 5,162,051
[45] Date of Patent: Nov. 10, 1992

[54] PHOTOEIOREACTOR

[75] Inventor: Scot D. Hoeksema, Elkridge, Md.

[73] Assignee: Martek Corporation, Columbia, Md.

[21] Appl. No.: 734,094

[22] Filed: Jul. 23, 1991

Related U.S. Application Data

[63] Continuation of Ser. No. 440,084, Nov. 22, 1989, abandoned.

[51] Int. Cl.$^5$ .................... A01G 7/00; A01H 13/00; F21V 33/00; C12M 1/04
[52] U.S. Cl. .................... 47/1.4; 362/101; 362/805; 422/186; 422/186.3; 435/287; 435/313; 435/314; 435/316
[58] Field of Search .................... 47/1.4, 17; 362/32, 362/122, 805, 101; 422/186, 904, 186.3; 435/173, 257, 287, 290, 313, 314, 316, 946; 250/436

[56] References Cited

U.S. PATENT DOCUMENTS

| | | |
|---|---|---|
| 3,986,297 | 10/1976 | Ichimura et al. ............ 47/1.4 |
| 4,233,958 | 11/1980 | Heden ...................... 47/1.4 |
| 4,253,418 | 11/1981 | Lockwood et al. .......... 47/1.4 |
| 4,555,864 | 12/1985 | Mori ....................... 47/1.4 |
| 4,626,065 | 12/1986 | Mori ....................... 47/1.4 |
| 4,676,956 | 6/1987 | Mori ....................... 47/1.4 |
| 4,724,214 | 2/1988 | Mori ....................... 47/1.4 |
| 4,900,678 | 2/1990 | Mori ....................... 47/1.4 |

FOREIGN PATENT DOCUMENTS

| | | |
|---|---|---|
| 084325 | 7/1983 | European Pat. Off. . |
| 103729 | 3/1984 | European Pat. Off. . |
| 85057041 | 12/1980 | Japan . |
| 57-113883 | 7/1982 | Japan . |
| 505405 | 5/1976 | U.S.S.R. ........ 47/1.4 |

OTHER PUBLICATIONS

Radmer et al., "An Analysis of the Productivity of a Continuous Algal Culture System", *Biotech & Bioeng.*, 29, (1987).
Lee, Y. K., "Enclosed Bioreactors for the Mass Cultivation of Photosynthetic Microorganisms: The Future Trend"; *Tibtech*, Jul. 1986, pp. 186-189.
Mori et al., "Sunlight Supply System and Gas Exchange in Microalgal Bioreactor System", *Adv. in Space Res.*, 1986, (McElroy and Shoog, eds.).
"An Introduction", TIR Systems Ltd., Jul. 1, 1985, 24 pages.

*Primary Examiner*—Howard J. Locker
*Attorney, Agent, or Firm*—Rothwell, Figg, Ernst & Kurz

[57] ABSTRACT

A photobioreactor for the cultivation of photosynthetic microorganisms is disclosed wherein a plurality of baffles are mounted in the photobioreactor tank forming hollow cavities which enable the insertion of light sources through openings in the tank wall. The baffles shield the light sources housed therein from the liquid photosynthetic culture contained in the tank thus facilitating electrical connections with the light sources and the maintenance thereof as well.

21 Claims, 3 Drawing Sheets

PHOTOBIOREACTOR

This is a continuation of application Ser. No. 07/440,084, filed Nov. 22, 1989, now abandoned.

BACKGROUND OF INVENTION

Algae have been cultivated artificially for such diverse purposes as the production of food for animals and humans, the treatment of sewage and waste waters, and the accumulation of radioactive wastes. More recently, algal cultures have been used for the production of enzymes having industrial and research applications and for producing oils and other materials having nutritional value. Modern biotechnology offers an opportunity for the genetic modification of algae to yield cultures capable of producing a wide variety of useful materials.

Various methods and equipment have been employed for the artificial culturing of algae. Perhaps the simplest procedures have involved the use of shallow open ponds exposed to sunlight. Such ponds are subject to contamination by dust, other microorganisms, insects and environmental pollutants and provide minimal ability to control the degree of exposure to light, temperature, respiration and other important factors. A more sophisticated approach has involved growing algal cultures in plastic-covered trenches and ponds, optionally having electrically powered pumps and agitators. These configurations reduce the chances of contamination of the culture and permit more accurate control of temperature, respiration and other parameters. Such configurations are still quite inefficient in terms of providing adequate and uniform amounts of light to the algal cells, particularly when sunlight is the sole source of light.

Unlike other microorganisms, the nutrient requirements of algae are very inexpensive, carbon dioxide being the principal source of carbon. On the other hand, the photosynthetic process requires that the algae be exposed to a relatively constant and uniform source of light. A primary design factor for modern photobioreactors involves providing a means for uniformly exposing the cells in the algal culture to the optimum amount of visible light. Like many plants, algae are quite sensitive to the amount and kind of light. Excessive light intensity can damage and kill algal cells. Too little light results in low levels of photosynthesis and consequently reduces growth.

A number of design factors are affected by the means selected for supplying light to the cells. For example, light sources, including natural sunlight, often emit substantial amounts of heat. Algal cultures are sensitive to heat and many of them grow most efficiently at temperatures of 20°-35° C. Thus, means must often be provided for cooling the algal culture and dissipating heat generated by the light source.

Two design factors closely related to the requirement for a uniform and constant supply of light are the cell density and the light path length. Like conventional fermentation processes, it is usually desirable to use as high a cell density as possible. Many of the same considerations apply to algal cultures as to bacterial cultures. For example, in addition to the light requirements, one must take into account the competition for nutrients, respiratory demands, viscosity and pumpability of the culture medium, and the like. However, an extremely high cell density results in cells more than a few millimeters from the light source being effectively shielded from the light. Simply increasing light intensity will not overcome this problem, because highly intense light will damage or kill cells near the light source.

The only effective way of increasing cell densities while maintaining a uniform amount of light is to employ a relatively short light path length. Of course, the requirement that the photobioreactor have a relatively short light path length introduces a new set of design problems. For industrial applications, it is usually desirable to employ high-volume microbial cultures. Large culture volumes are amenable to continuous or large-scale batch recovery operations and generally result in economies of scale. Satisfying the requirements for large culture volumes and short light path lengths has required that the photobioreactor have large, transparent walls which are closely spaced to define a light path and a fluid chamber within which the algal culture is contained. The transparent walls are illuminated with an appropriate light source to sustain the growth and photosynthetic reactions of the cells.

Various designs of such photobioreactors have been employed. A relatively simple design which has been successfully used in laboratory and pilot plant operations is simply a glass chamber having large, flat, parallel side walls and a narrow bottom and end walls. A gas sparging tube is placed in the bottom of the chamber to allow carbon dioxide or carbon-dioxide-enriched air to be sparged through a culture medium contained in the chamber, and banks of fluorescent light tubes are arranged adjacent to the side walls of the chamber. Inocula, nutrients, buffers, and the like can be introduced into the chamber through the top which may optionally be covered with a lid. This design has been very successful and useful for small scale operations.

An alternative embodiment of a bioreactor employing a fluorescent tube involves a cylindrical culture chamber having glass walls which surround a single fluorescent tube. The culture chamber may also be surrounded by a concentric cylindrical water jacket for controlling the temperature of the culture. Such a photobioreactor is described by Radmer, R., Behrens, P., and Arnett, L., in a paper titled "An Analysis of the Productivity of a Continuous Algal Culture System", published in *Biotechnology and Bioengineering*, 29 (1987), pp. 488-492. This design has also proven very valuable for laboratory-scale algal culturing operations, but, for many of the reasons described above, has not proven particularly useful for large-scale operations.

Various photobioreactors designs are reviewed in an article by Yuam-Kum Lee, "Enclosed Bioreactors for the Mass Cultivation of Photosynthetic Microorganisms: The Future Trend", *TIBTECH*, Jul. 1986, pgs. 186-189.

Furthermore, several problems have resulted from photobioreactor designs which have utilized light banks and light compartments immersed in the liquid microbial culture. Firstly, it is difficult to safely and effectively make the necessary electrical connections with the light tubes. Secondly, access to the light tubes for maintenance is made more difficult.

A significant need still exists for large-scale photobioreactors which are capable of using high intensity, low-cost lamps which provide uniform distribution of light over large surface areas while utilizing a safe and less complicated means for providing electrical power.

SUMMARY OF THE INVENTION

The present invention, in accordance with one embodiment thereof, comprises a novel photobioreactor in which at least one and preferably a plurality of light transmitting baffles are mounted side by side in a tank containing a liquid microbial culture. Each baffle is formed with a hollow cavity and is mounted so that the cavity is accessible from outside the tank for the insertion of a light source. The sides of the baffles are constructed of optically transparent material to transmit the light from the light source to the liquid which is in contact with the outside surfaces of the baffles. Each light source is made up of a plurality of light tubes, preferably fluorescent lamps, supported by braces or similar supporting structures and mounted in the baffles. Electrical leads are extended from the tubes to allow connection with an external power source.

In another embodiment, a single high intensity light source is mounted in a light compartment having walls made of internally reflective prismatic sheet material to provide uniform light of a suitable intensity to the microbial liquid culture.

The invention thus provides for greatly simplified electrical circuitry and connections, and reduces maintenance costs. Enabling access to the light sources from outside the tank and shielding the light sources from actual contact with the microbial culture makes it easier to identify and replace burned bulbs and it reduces the risks of short circuits as well.

Furthermore, as the light transmitting baffles are surrounded on its major light emitting surfaces by the liquid microbial culture, the spacing between adjacent tubes as well as between adjacent baffles is such as to optimize absorption of the emitted light by the algae and to assure virtually complete absorption of the emitted light.

In addition, the light transmitting baffles also perform a structural function in that their external surfaces serve as walls or draft spaces to define circulation paths through which the algae is moved by means such as air lift agitation. The baffles also form basic building blocks or modules which can be used in combination in any desired number for large scale photobioreactor systems of any selected capacity.

DETAILED DESCRIPTION OF THE INVENTION

Figure 1:
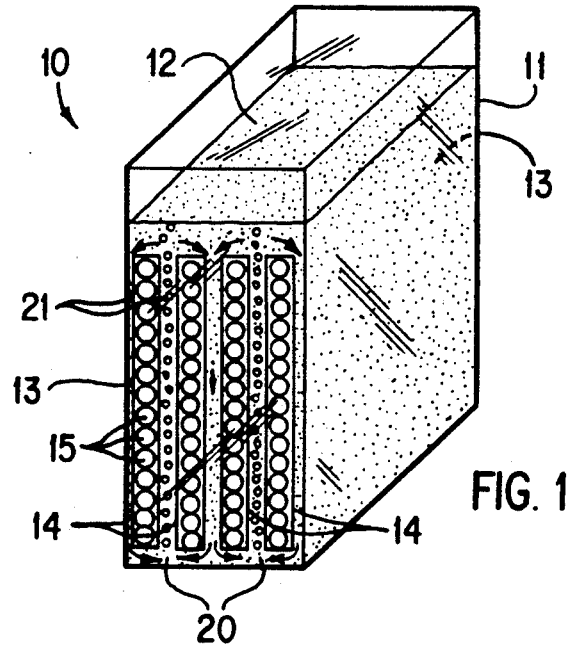
FIG. 1 is a perspective view of the photobioreactor illustrating an embodiment of the present invention.

Referring now to the drawings, FIG. 1 is a perspective view of a photobioreactor 10 embodying the present invention to be used in the culturing of dispersed cells or cell aggregates or multicellular organisms having a light requirement. As an example, this photobioreactor may be used to grow unicellular algae which carry on photosynthesis. The exterior of the photobioreactor 10 is in the form of a tank 11 capable of containing a liquid culture medium as illustrated by numeral 12. The liquid culture medium is sometimes referred to as an "algal" culture, but it will be appreciated that the photobioreactor 10 may be employed for the cultivation of any type of photosynthetic microorganism.

The basic unit of the photobioreactor is a rectangular tank 11 as shown in FIG. 1 with numerous internal baffles 14 which extend from one end of the tank to the other, and whose ends are sealed to the tank's inside walls. Each baffle 14 is formed with a hollow cavity which is accessible through openings in the wall of the tank. Tank end walls 13 can be cut out or molded in any conventional manner to enable access to the baffle cavities from outside the tank's end wall surface.

From the outer surface of the tank walls are openings permitting access to the cavity of the baffle for the insertion of a light source. In the embodiment shown in FIG. 1, a plurality of light tubes 15 are inserted into the baffle cavity from outside the tank's surface and housed therein. Baffles 14 serve to protect light tubes 15 from direct contact with the liquid culture medium 12. Light is therefore emitted substantially uniformally from tubes 15 and is absorbed by the algal culture.

Although the embodiment illustrated in FIG. 1 shows a rectangularly shaped tank 11, it is recognized that any convenient shape may be used.

The tank and baffle structure of the present invention is an improvement over the photobioreactor disclosed in pending application Ser. No. 07/163,800, (now U.S. Pat. No. 5,104,803) incorporated herein by reference, which discloses a compartment for protecting a light bank against fluid communication with a liquid culture medium. Permitting insertion of a light source into the baffle cavities through the tank's outer surfaces, as in the present invention, greatly facilitates electrical connectors to the light source and maintenance as well.

Located outside the tank 11 is means to control the temperature of the contents. A preferred means for controlling the temperature include water jackets or internal heat transfer coils which can be connected to refrigeration units (not shown) or heating units (not shown). Also, the dissolved oxygen and pH levels of the contents are continuously monitored and controlled by any conventional, well known means.

Figure 2:
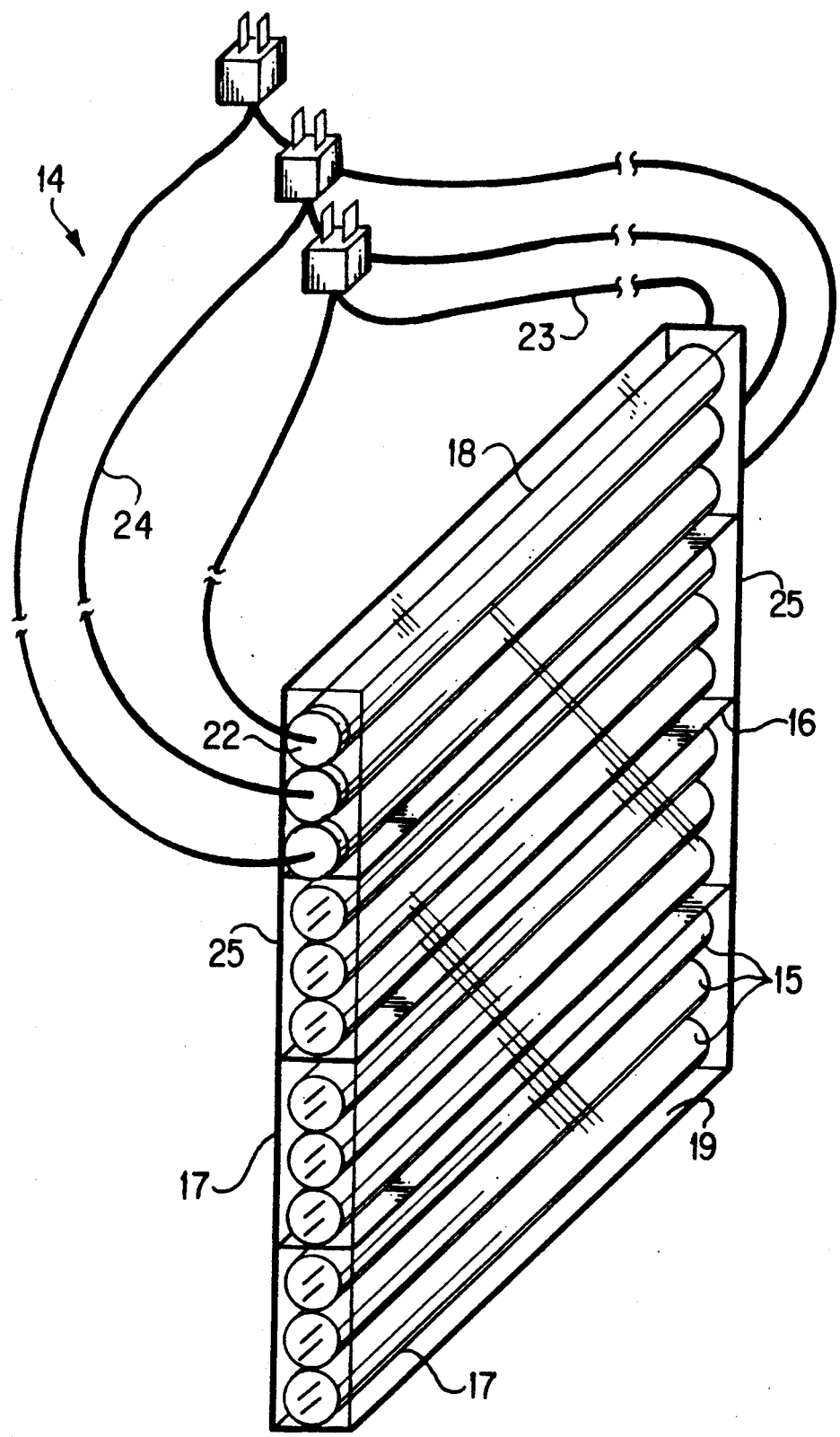
FIG. 2 is perspective view of a baffle and fluorescent tube arrangement forming part of the photobioreactor of FIG. 1.

FIG. 2 is a perspective view of a baffle 14 and the housing of light tubes 15 therein. Side panels 17 are substantially planar walls forming the baffle cavity therebetween. Planar walls 17 are major surfaces on the opposite sides of the cavity for the emission of light into said cavity. Side panels 17, top panel 18 and bottom panel 19 are made of a chemically inert and optically transparent material such as glass or acrylic. Internal braces 16 are mounted to facilitate placement and to support light tubes 15 or a bank of light tubes. Open baffle ends 25 permit the simple insertion of tubes through either end even while the photobioreactor is in an operational state as shown in FIG. 1.

In the embodiment shown in FIG. 2, light tubes 15 are fluorescent tube lamps essentially in their "off the shelf" condition without any modification or customization. The advantages of such lamps in this embodiment are that light is emitted from them substantially uniformly along the length of the tubes and in all directions perpendicular to the tubes. This, along with the particular baffle spacing, enables optimum absorption of the light by the algal culture.

Because end sections 25 of baffle 14 are open, electrical connections can easily and safely be made to light tubes 15 at their opposite ends in any conventional, well known way. As shown in FIG. 2, individual connections are made to each fluorescent tube 15 by members 22 whereby leads are brought out through wires 23 and 24 which terminate in an electrical plug connectable to a source of electric power (not shown). Suitable ballasts (not shown) are provided as well. These connections could also be made by providing a single adapter on each end section of the baffle or by grouping the tubes in any number.

In an alternative embodiment of the present invention, only one end of the baffle cavity is opened to the tank's outside surface. This structure would require running the lead wires connecting the fluorescent tubes at the closed end through the baffle cavity to the open end.

Figure 3:
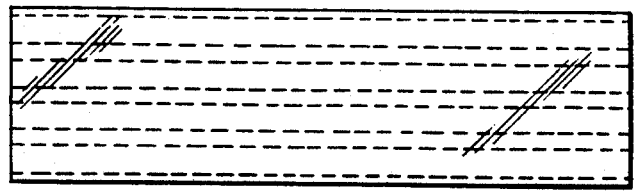
FIGS. 3-5 are top, end, and side views respectively of the photobioreactor illustrating the present invention.
Figure 5:
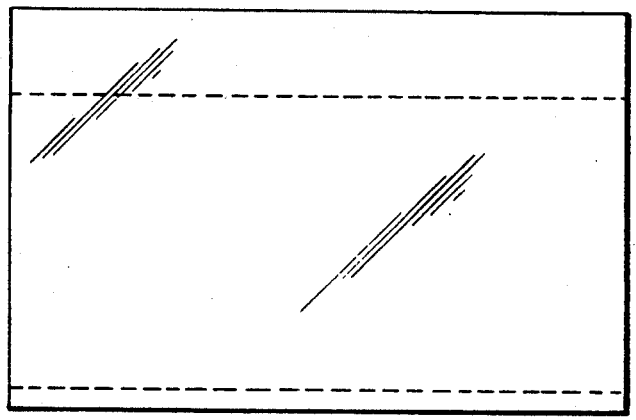
Figure 4:
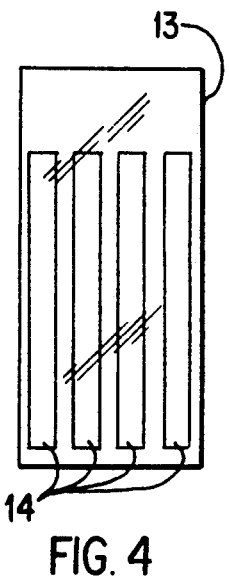

As mentioned above, the tank and baffle dimensions are selected to optimize light absorption by the algae culture during the photobioreactor's operation. According to one embodiment, as illustrated in FIGS. 3-5, baffles 14 are constructed to be 2 inches wide to enable the insertion of a fluorescent tube. The overall height of the baffles is determined by the number of fluorescent tubes to be inserted. In this embodiment, the height is approximately 24 inches which, as shown in FIG. 2, allows for 12 fluorescent tubes and three braces 16. The outer surfaces of adjacent baffles are separated by a distance of 1 inch, and one-half inch separates a baffle's outer surface and the tank wall. Baffles 14 will generally extend along the entire 48 inch tank length as illustrated in FIG. 5. The overall height and width of the tank in this embodiment are 31 inches and 12 inches as shown in FIGS. 4 and 3 respectively. Using high output, cool white fluorescent tubes, this spacing provides a near optimal light source for micro algae.

Furthermore, as illustrated in FIGS. 2-5, planar walls 17 form a major portion of the light emitting surfaces of the baffle. In accordance with the baffle dimensions set forth in the preferred embodiment described above, approximately 90% of the light emitted by the fluorescent tubes 15 is transmitted through planar walls 17. These figures are not intended to be limitations but are provided only to illustrate that planar walls are major surfaces forming a major portion of the baffle light emitting surfaces.

The particular tank and baffle dimensions shown in FIGS. 3-5 are for illustrative purposes only. It is to be recognized that the baffle widths and spacing between adjacent baffles will depend upon the photon flux of the light source, the optical properties of the baffle walls and the cell density of the culture being used. Furthermore, the photobioreactor can easily be constructed in any volume due to the tank's internal symmetry of the light-transmitting baffles. The photobioreactor in FIG. 1 has a working volume of 110-130 liters. This volume can easily be increased by widening the tank, increasing the height and increasing the number of baffles. Such a change in the photobioreactor design does not affect the operation or performance of the photobioreactor in any way.

Figure 7:
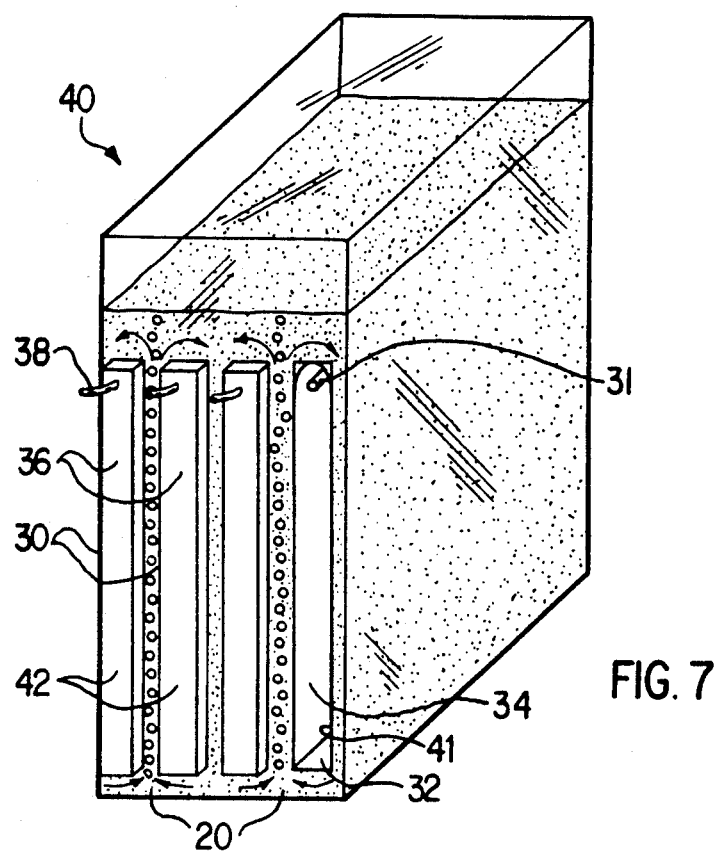
FIG. 7 is a perspective view of the photobioreactor illustrating the present invention utilizing the light source of FIG. 6.

As mentioned above, the light transmitting baffles also perform a structural function in that their external surfaces serve as walls or draft spaces to define circulation paths for the algal culture. As shown in FIG. 1, baffles 14 are mounted in the tank to form passages 21 therebetween to enable the culture circulation and to enhance the growth process. In order to promote circulation and agitation within the tank, a series of hollow tubes or cylinders 20, preferably formed of a metal or ceramic material or inert material, are placed, in the preferred embodiment, between alternate pairs of baffles as illustrated in FIG. 1. The cylinders 20 can also be positioned between any adjacent baffles at any vertical position or between the baffle and the tank wall. Furthermore, cylinders 20 can be placed just below the baffles such that substantially all the gas flows therebetween as illustrated in FIG. 7.

The cylinders 20 contain small perforations or apertures extending through the walls thereof forming gas sparging tubes through which a pressurized gas (e.g. carbon dioxide) is supplied for the photosynthesis requirements of the algal culture. The gas may be air or nitrogen or another inert gas either singly or enriched with carbon dioxide. As gas is bubbled into the culture, it forces the medium to rise creating a circulation up one channel and down another in the directions shown by the arrows in FIG. 1. It is recognized, however, that the up and down circulation as illustrated is not necessary to achieve mixing. Positioning the sparging tubes between adjacent baffles and between a baffle and tank wall will also achieve this desired result. Other means for supplying nutrient source gases and for circulating the culture may also be used.

Because the baffles extend through the entire length of the tank and the hollow cavities formed therein are accessible from the outer surface of the tank walls on either side, supplying electrical connections to the fluorescent tubes housed therein is greatly simplified. Providing maintenance for the tubes is simplified as well. Electrical leads connected to the ends of the tubes are made in the simple conventional manner and are completely shielded from the liquid culture 12. Recognition and replacement of burned light tubes is greatly facilitated by this novel structure. Furthermore, by selecting the proper light path lengths as described above, virtually 100% of the emitted light is absorbed by the culture and the light absorption is relatively uniform and optimized throughout the culture as well.

Figure 6:
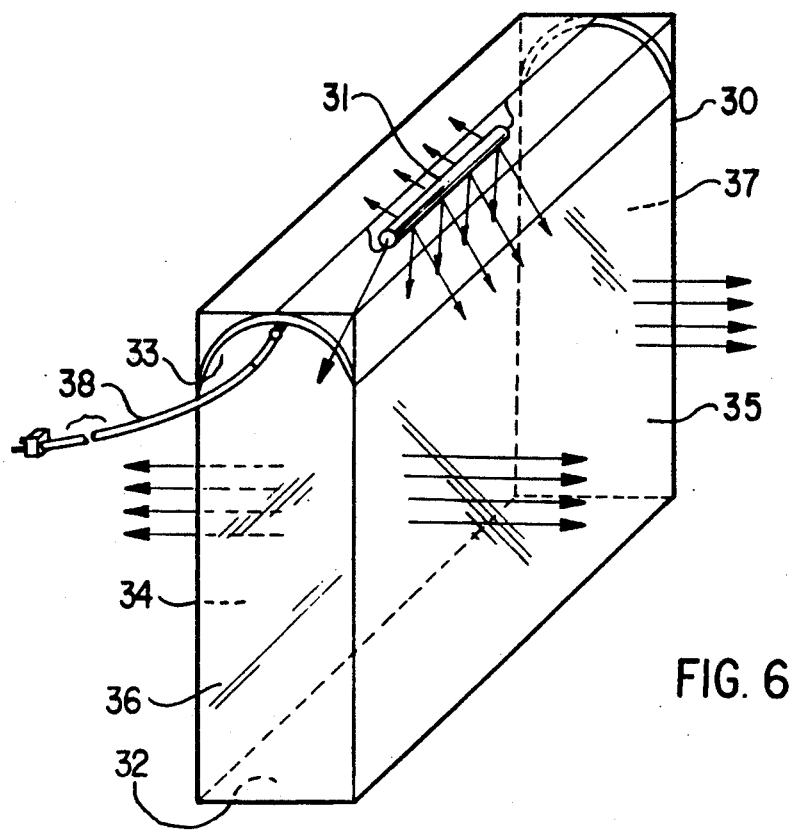
FIG. 6 is a perspective view of an alternate light source for the photobioreactor illustrating another embodiment of the present invention.

In accordance with another embodiment of the invention, as illustrated in FIG. 6, the light source is a single concentrated high-intensity light 31 mounted in a light compartment 30 to provide uniform high intensity light to the microbial liquid culture. Light compartment 30 contains means for substantially uniformly distributing light from source 31 with reflector 33 across the interior surface of transparent walls 34 and 35. Such means maybe in the form of a light guide constructed of internally reflective prismatic sheet material (not shown). The internally reflective prismatic sheet material is formed from highly transparent flexible sheet material, such as polyacrylate, on the surface of which is inscribed with minute 90° corrugations. As a result of these corrugations, light striking the sheet with an angle of incidence of about 27° or less will be reflected with nearly 100% efficiency. Minor imperfections in the prismatic sheets as well as light infringing the sheets at angles greater than about 27° result in transmission of light through the prismatic sheet material.

As shown in FIG. 6, a mirror 32 is located at the bottom of light compartment 30. As a result of the internal reflectance of the prismatic sheet material, reflectance of mirror 32 and reflector 33, light from the light source 31 is, to a large extent, reflected back into the compartment. The net result of this internal reflectance is that the light from the light source is distributed substantially uniformly across the inner surface of wall 33 and thus provides a highly controlled distribution of light throughout the light paths in the walls 34 and 35. Light from the light source is therefore emitted and distributed substantially uniformally from the exterior surfaces of the baffle's planar walls.

Since it is not desirable to have light emitted from end surfaces 36 and 37, a reflective cover (not shown) is placed between the compartment wall and the internally reflective prismatic sheet so that the light is redirected back into the compartment. Mirrors may be used as end surfaces 36 and 37 as well. Furthermore, light source 31 could be placed near end surfaces 36 and 37 in vertical arrangement to effect the uniform emittance. Constructing a light compartment utilizing a prismatic sheet material and the light guides formed therefrom is described in U.S. patent application Ser. No. 07/338,532, incorporated herein by reference.

The electrical power can be supplied to the high intensity light source 31 in any conventional manner. As illustrated in this embodiment, leads connected to source 31 are brought out through wire 38 and terminate in an electrical plug connectable to a source of electric power (not shown).

FIG. 7 shows a perspective view of the photobioreactor utilizing the light source 30. Photobioreactor 40 operates in an identical way as described with reference to photobioreactor 10. Baffles 41 are formed with hollow cavities extending the entire tank length and are constructed to enable the insertion of the light source from the either or both ends of the tank, through open ends 42. Electrical connections to source 30 are very simply made in any well known, conventional way as described above.

While it is apparent that the preferred embodiment shown and described provides certain advantages, many of the advantages of the present invention can nevertheless be realized in other configurations, and it will be appreciated that various modifications, changes and adaptions can be made, all of which are intended to be comprehended within the meaning and range equivalents of the appended claims.

What is claimed is:

1. A photobioreactor comprising:
   (a) a tank for containing a liquid photosynthetic culture at a preselected operating level within said tank;
   (b) a plurality of baffles each extending from one tank wall to an opposite tank wall, each of said baffles comprising optically transparent and generally planar walls having exterior light emitting surfaces and forming a liquid impervious hollow cavity therebetween;
   (c) means for mounting said baffles within said tank such that the hollow cavity in each of said baffles is accessible from outside the tank wall which enables the insertion of a light source in said hollow cavity in each of said baffles without the need for accessing the interior volume of the photobioreactor; and
   (d) means for positioning said baffles in said tank spaced apart with said planar walls in generally parallel relation with each other;
   wherein said planar walls positioned in generally parallel relation establish available flow paths for the culture and enable the culture to be exposed to a substantially uniform light distribution.

2. The photobioreactor as set forth in claim 1 wherein said means for positioning comprises means for spacing apart said baffles such that substantially all the light emitted from the exterior surfaces is absorbed in the culture.

3. The photobioreactor as set forth in claim 1 wherein said means for mounting comprises sealing ends of said baffles to the tank walls and wherein said cavities are accessible through an opening in at least said one tank wall.

4. The photobioreactor as set forth in claim 1 wherein said light source is a plurality of fluorescent tubes.

5. The photobioreactor as set forth in claim 1 including means for introducing a sparging gas to flow between at least some of said baffles.

6. The photobioreactor as set forth in claim 5 wherein said means for introducing a sparging gas is positioned between at least some of said baffles.

7. The photobioreactor as set forth in claim 4 including means for connecting said fluorescent tubes with an electrical power supply.

8. The photobioreactor as set forth in claim 4 wherein each of said baffles comprises at least one spacer for separating and supporting said fluorescent tubes.

9. The photobioreactor as set forth in claim 3 wherein said light source is insertable into said cavity through an opening in said one tank wall and said opposite tank wall.

10. The photobioreactor as set forth in claim 1 wherein substantially all light emitted into said liquid photosynthetic culture is emitted through said light emitting surfaces of said planar walls.

11. The photobioreactor as set forth in claim 10 wherein each of said baffles is approximately two inches in width and 24 inches in height.

12. The photobioreactor as set forth in claim 2 wherein outer surfaces of adjacent baffles are separated by a distance of approximately one inch.

13. The photobioreactor as set forth in claim 1 wherein said light source is a high intensity light source directed into a light compartment;
   said light compartment comprising an internally reflective prismatic sheet extending substantially from said light source to an end wall opposite said light source, said compartment further comprising a mirror at an end opposite said light source oriented to reflect light back into said compartment wherein said light source, said reflective prismatic sheet and said mirror are arranged such that light from said light source is distributed and emitted substantially uniformly from the exterior surfaces of said planar walls.

14. The photobioreactor as set forth in claim 1 wherein said tank and said baffles are generally rectangular in shape.

15. The photobioreactor as set forth in claim 1 wherein said light source is an array of fluorescent tubes positioned horizontally within said hollow cavity.

16. The photobioreactor as set forth in claim 1 wherein said light source is insertable through an opening in a side wall of said tank.

17. The photobioreactor as set forth in claim 1 wherein said means for mounting comprises sealing ends of said baffles to the tank walls and wherein each of said cavities is accessible through an opening in a side wall of said tank.

18. A photobioreactor comprising:
(a) a tank for containing a liquid photosynthetic culture;
(b) a plurality of light compartments each containing a high intensity light source;
(c) a plurality of baffles mounted within said tank extending from one tank wall to an opposite tank wall and positioned in generally parallel relation to each other, each said baffle comprising substantially planar and optically transparent surfaces forming a hollow cavity which is accessible through an opening in the tank wall and enables the insertion of said light compartments into said cavity of each of said baffles without the need for accessing the interior volume of the photobioreactor; and
(d) said light compartment comprising means for emitting and distributing light from said high intensity light source substantially uniformly from the exterior surfaces of said planar surfaces;
wherein said planar walls are positioned in generally parallel relation to each other to establish available flow paths for the culture and enables the culture to be exposed to a substantially uniform light distribution.

19. The photobioreactor as set forth in claim 18 wherein said means for distributing and emitting light comprises an internally reflective prismatic sheet material extending substantially from said light source to an end wall opposite said light source and a mirror at an end opposite said light source oriented to reflect light back into said compartment.

20. The photobioreactor as set forth in claim 18 including means positioned between at least some of said baffles for introducing a sparging gas.

21. The photobioreactor as set forth in claim 18 including means for connecting said high intensity light source with an electrical power supply.

* * * * *

UNITED STATES PATENT AND TRADEMARK OFFICE
CERTIFICATE OF CORRECTION

PATENT NO. : 5,162,051
DATED : November 10, 1992
INVENTOR(S) : Scot D. Hoeksema

It is certified that error appears in the above-indentified patent and that said Letters Patent is hereby corrected as shown below:

On the title item [54] and in column 1, line 2, the title should read --PHOTOBIOREACTOR--.

Signed and Sealed this

Twenty-eighth Day of June, 1994

Attest:

BRUCE LEHMAN

*Attesting Officer*  *Commissioner of Patents and Trademarks*